United States Patent [19]

Furlan

[11] Patent Number: 4,562,191

[45] Date of Patent: Dec. 31, 1985

[54] METHYL-PIPERAZINO DERIVATIVES WITH ANALGESIC ACTIVITY

[75] Inventor: Diego Furlan, Segrate, Italy

[73] Assignee: Euroresearch S.R.L., Milan, Italy

[21] Appl. No.: 667,714

[22] Filed: Nov. 2, 1984

[30] Foreign Application Priority Data

Nov. 15, 1983 [IT]  Italy ................................ 23720 A/83

[51] Int. Cl.⁴ .................... A61K 31/495; C07D 241/04
[52] U.S. Cl. ....................................... 514/255; 544/391
[58] Field of Search ......................... 544/391; 514/255

[56] References Cited

U.S. PATENT DOCUMENTS

| | | | |
|---|---|---|---|
| 2,882,271 | 4/1959 | Janssen | 544/391 |
| 3,318,876 | 5/1967 | Cignarella et al. | 544/391 |
| 3,625,965 | 12/1971 | Irikura et al. | 544/391 |
| 4,041,038 | 8/1977 | Irikura | 544/391 |
| 4,178,442 | 12/1979 | Bourgery et al. | 544/391 |
| 4,368,199 | 1/1983 | Ancher et al. | 544/391 |
| 4,492,698 | 1/1985 | Björk et al. | 544/391 |

FOREIGN PATENT DOCUMENTS 2623772  12/1976  Fed. Rep. of Germany ...... 544/391

*Primary Examiner*—Glennon H. Hollrah
*Assistant Examiner*—James J. Turnipseed
*Attorney, Agent, or Firm*—Stevens, Davis, Miller & Mosher

[57] ABSTRACT

New methyl-piperazino derivatives of formula:

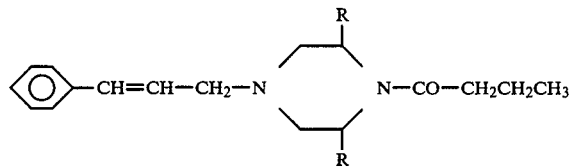

where R is H or methyl, at least one R being methyl.

These products are excellent analgesics with peripheral and central activity, and are free from side effects.

2 Claims, No Drawings

METHYL-PIPERAZINO DERIVATIVES WITH ANALGESIC ACTIVITY

This invention relates to new methyl-piperazino derivatives of general formula:

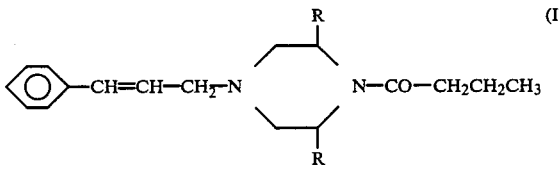

where R is H or methyl, at least one R being methyl, and to the corresponding salts obtained by salifying the basic compound with a pharmaceutically acceptable acid such as hydrochloric, sulphuric or tartaric.

The two new compounds of formula (I), ie N-butyryl-N'-cinnamyl-2-methyl-piperazine and N-butyryl-N'-cinnamyl-2,6-dimethyl-piperazine, possess intense analgesic activity both of central and peripheral type, are free from side effects, do not give rise to dependence phenomena, and possess low toxicity.

The compounds of formula (I) are prepared by reacting in a first stage the starting methyl-piperazino compound, ie either 2-methyl-piperazine or 2,6-dimethyl-piperazine, with cinnamyl chloride in an inert organic solvent, and then separating the cinnamyl-piperazine from the reaction mixture by extraction with acidified water.

The cinnamyl-piperazine intermediate is then reacted with butyryl chloride in an inert solvent, in an anhydrous environment in the presence of a base. The final product is then separated from the reaction solvent in the form of the hydrochloride.

A more detailed description of the preparation of the compounds according to the invention is given hereinafter by way of example.

SYNTHESIS OF N-BUTYRYL-N'-CINNAMYL-2-METHYL-PIPERAZINE HYDROCHLORIDE 34.6 g (0.2M) of 2-methyl-piperazine dihydrochloride suspended in 200 ml of isopropanol are fed into a 500 ml, three-neck flask fitted with a magnetic agitator, a bulb-type reflux condenser with a $CaCl_2$ plug, a thermometer and a dropping funnel, and 21.3 g (0.2M) of 94% 2-methyl-piperazine are added under strong agitation.

Agitation is continued at ambient temperature until complete dissolution is obtained. Dissolving time about one hour. The mixture is then heated to 65° C., and 32 g (0.2M) of 95% cinnamyl chloride dissolved in 50 ml of isopropanol are dripped in under strong agitation. Addition time about 20 minutes. When this addition is complete, agitation is continued for 45 minutes at 65° C., and then for 12 hours at ambient temperature. A suspension is obtained which is filtered under vacuum. The solid residue separated in this manner consists of 31 g of pure 2-methyl-piperazine dihydrochloride. The filtrate is evaporated to dryness under low pressure, taken up in benzene and water and acidified to pH 1.5 with concentrated HCl. It is agitated for 15 minutes and the phases are then separated. Aqueous phase is adjusted to pH 11 with 10% NaOH and extracted three times with 150 ml of benzene.

The phases are separated, and the pooled organic phases are dried with anhydrous sodium sulphate and filtered.

18.20 g (25 ml, 0.18M) of dimethylamine are added to the clear solution obtained, and then 18.1 g (0.17M) of butyryl chloride are dripped in under strong agitation while maintaining the reaction temperature at ≦25° C. Addition time about 15 minutes.

The mixture is left under agitation at ambient temperature for 12 hours, after which 100 ml of cold water are added and the mixture adjusted to pH 1.5 with concentrated HCl. In this manner, a rubbery precipitate is obtained which is filtered off, washed with 50 ml of benzene and dried at 50° C. under vacuum.

38 g of product of 95% purity are obtained in this manner.

The product is crystallised from 300 ml of acetonitrile to obtain 30 g of white product having the following characteristics:

| | | | |
|---|---|---|---|
| white crystalline powder M.P. 211°–213° C. n.c. | | | |
| TLC single machine | eluent | butanol | 80 |
| | | water | 10 |
| | | acetic acid | 10 |
| Purity 100% | | | |
| molecular weight 322.5 | | | |
| IR characteristic band at 1625 nm | | | |
| formula $C_{18}H_{26}N_2O \cdot HCl$ | | | |
| elementary analysis | | | |

| | Calculated | Found |
|---|---|---|
| C | 66.90% | 66.62% |
| H | 8.36% | 8.59% |
| N | 8.67% | 8.67% |

SYNTHESIS OF N-BUTYRYL-N'-CINNAMYL-2,6-DIMETHYL-PIPERAZINE HYDROCHLORIDE 37.4 g (0.2M) of 2,6-dimethyl-piperazine dihydrochloride suspended in 200 ml of isopropanol are fed into a 500 ml three-neck flask fitted with a magnetic agitator, a bulb-type reflux condenser with a $CaCl_2$ plug, a thermometer and a dropping funnel, and 23.5 g (0.2M) of 97% 2,6-dimethyl-piperazine are added under strong agitation.

The mixture is left under agitation at ambient temperature until complete dissolution has taken place. Dissolving time about 90 minutes. It is heated to 65° C. and 32 g (0.2M) of 95% cinnamyl chloride dissolved in 50 ml of isopropanol are dripped in under strong agitation. Addition time about 20 minutes. When the addition is complete, the mixture is left under agitation for 45 minutes at 65° C. and then for 12 hours at ambient temperature.

In this manner a slurry is obtained which is filtered under vacuum. The solid residue consists of 32 g of 2,6-dimethyl-piperazine dihydrochloride.

The filtrate is evaporated to dryness under low pressure and taken up in 150 ml of benzene and 150 ml of water and acidified to pH 1.5 with concentrated HCl. It is left under agitation for 15 minutes, after which the phases are separated. The aqueous phase is adjusted to pH 11 with 10% NaOH and extracted three times with 150 ml of benzene. The pooled organic phases are dried with anhydrous sodium sulphate and filtered. 18.2 g (25 ml, 0.18M) of triethylamine are added to the clear solution obtained, and then 18.1 g (0.17M) of butyryl chloride are dripped in under strong agitation while maintaining the reaction temperature at 25° C. Addition time about 15 minutes.

The mixture is left under agitation at ambient temperature for 12 hours, after which 100 ml of cold water are added, and the mixture acidified to pH 1.5 with concentrated HCl. In this manner a rubbery precipitate is obtained which is filtered off, washed with 50 ml of benzene and dried at 50° C. under vacuum.

30 g of product are obtained of 94% purity. The product is dissolved in 100 ml of acetonitrile, filtered over carbon and precipitated with 150 ml of ethyl ether. In this manner 21 g of product are obtained having the following characteristics:

white powder
M.P. 149°–151° C. n.c.
TLC single machine:  eluent  n. butanol  80
                             acetic acid 10
                             water       10
purity 100%
M.W. 345.85
IR characteristic band at 1630 nm
formula $C_{19}H_{28}N_2O \cdot HCl \cdot \frac{1}{2}H_2O$
elementary analysis

|   | Calculated | Found  |
|---|------------|--------|
| C | 65.92%     | 65.83% |
| H | 8.67%      | 8.70%  |
| N | 8.09%      | 8.15%  |

ANALGESIC PROPERTIES

The analgesic properties both of central and peripheral type were examined for the two compounds according to the invention, in comparison with known drugs of different structure, in comparison with two higher homologues, namely N-valeryl-N'-cinnamyl-2-methyl (and 2,6-dimethyl)-piperazine, and in comparison with a simpler compound not containing methyl groups, namely N-butyryl-N'-cinnamyl-piperazine.

Overall, it was found that the two compounds according to the invention have better pharmacological properties, and in particular an analgesic action of central type which is decidedly better than their homologues.

ANALGESIC ACTIVITY IN THE MOUSE

P-phenylbenzoquinone test (peripheral analgesia)

Method

Male CD-1 albino mice were used having a body weight of between 25 and 30 grams, and having been fasting for about 18 hours at the moment of treatment. The p-phenylbenzoquinone was prepared by dissolving 20 mg of the substance in a calibrated dark glass flask in 5 ml of absolute alcohol while heating in a water bath to 40° C., the final volume than being adjusted to 100 ml with saline solution (9% NaCl).

The phenylquinone thus prepared was used for a maximum of 4 hours, after which it was freshly prepared.

Groups of 6 animals were treated at a time with the products under examination by oral administration, and the p-phenylbenzoquinone was administered after 30 minutes in a quantity of 20 ml/kg of body weight intraperitoneally.

The contortions undergone in the next 20 minutes were then observed and counted.

The two compounds according to the invention, namely the monomethyl derivative indicated in Table 2 by the reference number 3 and the dimethyl derivative indicated by the reference number 4, were examined.

The table also shows for comparison purposes the results obtained with:

N-butyryl-N'-cinnamyl-piperazine, reference number 0

N-valeryl-N'-cinnamyl-2-methyl-piperazine, reference number 1

N-valeryl-N'-cinnamyl-2,6-dimethyl-piperazine, reference number 2 and also, as known reference analgesics, D-propoxyphene, phenylbutazone and acetyl salicyclic acid.

Results

Table 1 shows for each product and dose level the number of animals out of the total treated which underwent contortions, and the mean number of these contortions, but calculated only for the number of animals which underwent them.

From an analysis of the results it can be concluded that:

product 0 has good peripheral analgesic activity, this being total at a dose of 100 mg/kg by oral administration, whereas at the lower doses of 50 and 25 mg/kg by oral administration, only the number of contortions is lower, but not the number of animals undergoing them.

of the other products, the best in the absolute sense appear to be product 4 and product 3, these being active at all the tested doses of 100, 50 and 25 mg/kg by oral administration. The activity is most marked on the mean number of contortions, even though there is protection against contortions for 50% of the animals the activity of products 3 and 4 is slightly better than that of acetylsalicylic acid and phenylbutazone, and slightly worse than that of D-propoxyphene at a dose of 20 mg/kg by subcutaneous administration.

TABLE 1

| | P—phenyl-benzoquinone test | | |
|---|---|---|---|
| Product | Dose mg/kg | No. of animals exhibiting contortions out of total | Mean number of contortions ± S.D. |
| Controls | — | 18/18 (100%) | 21.8 ± 2.6 |
| 0 | 100 oral | 0/6 | 0.0 |
|   | 50 oral  | 6/6 | 8.0 ± 1.4 |
|   | 25 oral  | 5/6 | 4.2 ± 3.1 |
| 1 | 100 oral | 0/6 | 0.0 |
|   | 50 oral  | 2/6 | 2.0 ± 1.4 |
|   | 25 oral  | 5/6 | 16.0 ± 9.8 |
| 2 | 100 oral | 2/6 | 15.5 ± 7.8 |
|   | 50 oral  | 5/6 | 7.0 ± 5.2 |
|   | 25 oral  | 4/6 | 21.2 ± 10.6 |
| 3 | 100 oral | 2/6 | 5.0 ± 1.4 |
|   | 50 oral  | 3/6 | 3.3 ± 0.6 |
|   | 25 oral  | 4/6 | 11.5 ± 7.0 |
| 4 | 100 oral | 4/6 | 3.5 ± 2.4 |
|   | 50 oral  | 3/6 | 4.7 ± 4.7 |
|   | 25 oral  | 3/6 | 5.0 ± 1.7 |
| Acetyl-salicylic acid | 100 oral | 4/6 | 13.5 ± 11.1 |
| Phenyl-butazone | 100 oral | 3/6 | 2.7 ± 1.5 |
|   | 50 oral | 5/6 | 11.4 ± 11.0 |
| Propoxyphene | 20 s.c. | 2/6 | 2.5 ± 2.1 |

ANALGESIC ACTIVITY IN THE MOUSE

Hot plate test (central analgesia)

Method

Female CD-1 albino mice were used, having a body weight of between 20 and 25 grams. At the moment of commencing the experiment the animals were not in a state of fast, but remained fasting for the rest of the test.

The apparatus used for evaluating analgesic activity was the "Rova Ter" model of the firm Terzani. The plate temperature was kept constant at 54.5° C. The reaction time, in seconds, was measured when the animal showed obvious symptoms of pain at its rear paws, ie when the paws trembled and were withdrawn backwards, or were licked. As the reaction time for a normal mouse varies between 5 and 13 seconds, all the animals used in each experiment were selected for uniformity of reaction time.

For this purpose, the basic reaction time (r.t.) was measured twice for each animal at an interval of 15 minutes, and after a further 15 minutes the animals were treated with the products under examination. The reaction time was again measured 30 minutes and 60 minutes after the treatment.

The two compounds according to the invention were examined, namely the monomethyl derivative indicated in Table 2 by the reference number 3 and the dimethyl derivative indicated by the reference number 4. For comparison purposes, the table also shows the results obtained with:

N-butyryl-N'-cinnamyl-piperazine, reference number 0
N-valeryl-N'-cinnamyl-2-methyl-piperazine, reference number 1
N-valeryl-N'-cinnamyl-2,6-dimethyl-piperazine, reference number 2 and also D-propoxyphene as a known reference analgesic.

Three animals were used for each dose and type of administration, except for the D-propoxyphene, for which 15 animals per dose were used.

Results

Table 2 shows the mean reaction times (r.t.), namely the basic reaction times and those 30 minutes and 60 minutes after treatment, for each group and dose level. After the maximum reaction time considered, the animal was in any case removed from the plate, and the mean value has thus been indicated on the table by the sign >.

From the results obtained it can be concluded that:
the product 0 has good activity at doses of 100 and 50 mg/kg by subcutaneous administration, whereas it is not active at a dose of 100 mg/kg of oral administration, nor at 25 mg/kg by subcutaneous administration
the products 1 and 2 are not active either by oral administration (100 mg/kg) or by subcutaneous administration (100, 50 or 25 mg/kg)
the products 3 and 4 have very good analgesic activity both by oral administration (100 mg/kg) and by subcutaneous administration. The product 4 is undoubtedly better at a dose of 25 mg/kg whereas at the lower dose of 10 mg/kg the product 3 appears better. The activity is better at 30 minutes after treatment than at 60 minutes after treatment, although it is still very good. The analgesic activity of these products is without doubt better than that of the D-propoxyphene used as the reference test substance.

TABLE 2

Hot Plate Test

| PRODUCT | DOSE mg/kg | BASIC | REACTION TIMES AFTER 30 MIN | AFTER 60 MIN |
|---|---|---|---|---|
| 0 | 100 oral | 9.7 | 12.3 | 12.7 |
|  | 100 s.c. | 9.0 | 33.7 |  |
|  | 50 s.c. | 8.7 | 22.7 |  |
|  | 25 s.c. | 6.5 | 9.2 |  |
| 1 | 100 oral | 8.3 | 15.3 | 13.6 |
|  | 100 s.c. | 7.3 | 11.6 | 8.6 |
|  | 50 s.c. | 7.0 | 10.3 | 11.0 |
|  | 25 s.c. | 7.3 | 9.3 | 10.0 |
| 2 | 100 oral | 10.3 | 4.3 | 9.6 |
|  | 100 s.c. | 6.7 | 5.3 | 5.7 |
|  | 50 s.c. | 7.0 | 5.7 | 8.3 |
|  | 25 s.c. | 6.3 | 10.0 | 11.7 |
| 3 | 100 oral | 9.3 | >42 | 34 |
|  | 50 s.c. | 9.7 | >60 | >58 |
|  | 25 s.c. | 6.0 | 34.3 | 25.7 |
|  | 10 s.c. | 10.3 | 19.7 | 5.3 |
| 4 | 100 oral | 8.0 | >32 | 29.7 |
|  | 50 s.c. | 7.3 | 50.0 | >38 |
|  | 25 s.c. | 7.0 | >51 | >46 |
|  | 10 s.c. | 8.7 | 9.0 | 11.3 |
| D-propoxyphene * | 20 s.c. | 6.9 ± 0.7 | 13.8 ± 1.2 |  |
|  | 10 s.c. | 7.5 ± 0.7 | 14.4 ± 2.5 |  |

*15 animals per group

ACUTE TOXICITY IN THE CD-1 MOUSE (approximate $LD_{50}$ by the irving test)

Method

Animals: male and female CD-1 albino mice with a body weight of between 25 and 40 grams

Products and method of administration

For intravenous administration, all the compounds under examination were dissolved in physiological solution (9% NaCl) and inoculated into the retro-orbital sinus in a quantity of 10 ml/kg of body weight.

For oral and subcutaneous administration, the compounds were homogenised in a 5% gum arabic solution and administered in a quantity of 20 ml/kg of body weight.

The compounds examined and the reference numbers with which they are indicated hereinafter are the same as those already stated for the analgesic activity tests of Tables 1 and 2.

Doses: For oral and subcutaneous administration, doses of 1000, 500 and 300 mg/kg were used, whereas for intravenous administration doses of 70, 60, 50, 40, 30 and 20 mg/kg were used.

Number of animals: From a minimum of 3 males and 3 females to a maximum of 6 males and 6 females were used for each dose.

Observations made

Immediately after treatment and during the entire working day the animals were observed in accordance with the Irving test, ie their behaviour, humour, motor activity, action on the C.N.S., motor incoordination, muscular tone, reflexes and phenomena of the vegetative nervous system.

On the subsequent days up to the 7th, the animals were checked in the morning and mortality was recorded. The approximate $LD_{50}$ was calculated on the total mortality up to the 7th day by a simple arithmetic calculation.

Results

Table 3 shows the $LD_{50}$ values for each compound and method of administration. For intravenous administration all compounds have the same or only slightly different toxicity. Compound 3 appears the least toxic. For oral and subcutaneous administration, compounds 1, 2 and 4 have approximately the same toxicity without marked differences between the two methods of administration (at least up to the maximum used dose of 1000 mg/kg).

Compounds 0 and 3 are the most toxic, especially by oral and subcutaneous administration.

The individual compounds are considered hereinafter with regard to the symptomatology observed.

COMPOUND 0

Intravenous administration

At the higher doses of 70 and 60 mg/kg, stiffening of the body and tail, dyspnea (gasping), loss of posture and slight salivation were observed immediately after inoculation. Manifest convulsions were not observed, but only slight contractions of the rear limbs. Death occurred after between a few seconds and 10 minutes under complete muscular relazation.

At a dose of 50 mg/kg, twitching was observed immediately after inoculation, with short tonic convulsions, and dyspnea to the point of almost arresting breathing, followed by death within a few minutes under complete muscular relaxation. In some animals (those which did not die) the convulsions are more violent and more lasting, and of tonic-clonic type, being repeated at intervals of 2-3 minutes with jumping and stereotypy. About 4 hours after treatment, the animals reacquire nearly normal behaviour, and analgesic activity is no longer noted.

At the lower doses there is only stiffening of the tail with slight tonic convulsions, loss of posture or only Straub tail, and slightly abnormal walking.

Oral and subcutaneous administration

At a dose of 1000 mg/kg by oral administration, the animals present a symptomatology a few minutes after treatment which is analogous to that observed for intravenous administration, with slight tremor and tonic convulsions, dyspnea, loss of posture, tail stiffening, increase in abdominal tone, and positive reaction to acoustic but not to painful stimuli. With subcutaneous administration the symptomatology is the same, and death occurs about 15 minutes after treatment. At the lower doses, the symptomatology is approximately the same, and the product appears less toxic by subcutaneous administration. There is tail stiffening, increase in body tone, fur in disorder, arching of the back, weak and infrequent jumping and slight vocalisation, dilation of the pupil, little motor activity, abnormal walking, but normal reaction to touch.

Death occurs up to the 6th hour. Those animals which do not die after about 4 hours reacquire nearly normal behaviour, but central analgesia persists. In others, tremors, slight tonic convulsions and disordered fur persist, and a slight noise leads to sudden jumping. The animals lie immobile in this state either on their back or on a part of the body for at least 4 hours, after which they reacquire their straightening reflex and a progressive nearly normal hehaviour, but central analgesia persists.

On the day following treatment, all surviving animals have normal appearance and behaviour.

COMPOUND 1

Intravenous administration

The symptomatology observed is basically the same as that described heretofore. At doses of 70 and 60 mg/kg, death occurs a few seconds after inoculation under complete muscular relaxation, there being only slight stiffening of the tail, brief jumping and gasping (respiratory blockage). At a dose of 50 mg/kg the tonic-clonic convulsions are more manifest, and the animals die through respiratory blockage between 2 minutes and 10 minutes after treatment.

Central analgesia in the survivors persists for about 20 minutes. At a dose of 40 mg/kg there are slight tonic convulsions, dyspnea, stiffening of the tail, losses of posture, violent jumping after a few minutes, Straub tail, exaggerated response to acoustic stimulus with convulsions and violent jumping which cause the animal to leap out of its cage. This behaviour persists for about 10-15 minutes, after which the animals gradually reacquire almost normal behaviour. A slight analgesic activity is still present after one hour. At doses of 30 and 20 mg/kg the animals have only a slightly reduced behaviour, and motor activity and posture are also reduced. Central analgesia persists for about 15 minutes.

Oral and Subcutaneous administration

The symptomatology observed is basically the same as that described for compound 0. Mortality is observed between 10 minutes and 4 hours after treatment. At the end of the day all animals have reacquired nearly normal behaviour.

COMPOUND 2

Intravenous administration

The symptomatology is almost identical to that described heretofore, with the exception that an evident exophthalmos is also observed.

Oral and subcutaneous administration

No cases of death are observed for either method of administration, even at the maximum dose of 1000 mg/kg. During the day of treatment the animals seem slightly sedated but are of nearly normal appearance. In those treated orally, central analgesia is more marked.

COMPOUND 3

Intravenous administration

At a dose of 70 mg/kg and in those animals which die at a dose of 60 mg/kg there are immediate tonic convulsions with stiffening of the tail, increase in body tone, gasping, subsequent loss of posture and death due to respiratory blockage under complete muscular relaxation, within a few minutes after treatment.

At a dose of 50 mg/kg there is immediate jumping with tonic convulsions, dyspnea and gasping, stiffening of the body and tail, and an increase in the tone of the limbs. Touching produces brief tonic-clonic convulsions of low intensity, followed by violent jumping and excessive reaction to environmental stimuli, and central analgesia with Straub tail. Exophthalmos is not observed in these animals. At lower doses, immediately after inoculation there is jumping and psychomotor excitement, loss of posture, stiffening of the tail and limbs, dyspnea, abnormal walking, stereotypy and strong central analgesia.

Oral and subcutaneous administration

At a dose of 1000 mg/kg (oral and subcutaneous administration), immediately after inoculation the animals show evident psychomotor excitement with Straub tail, and contracting of the limbs which determines abnormal walking. Subsequently, the animals remain immobile lying on their back or on their side, with their limbs hypertonic, they react positively to acoustic stimuli with brief tonic convulsions, and dyspnea is present.

Mortality is observed between the 6th and 16th hour following treatment. There is an analogous symptomatology at the lower doses, and cyanosis is well observed at the tail and ear vessels. For equal doses the effects are much more evident with oral administration. A certain central analgesia persists up to three hours following treatment.

COMPOUND 4

Intravenous administration

At the higher doses of 70 and 60 mg/kg, immediately after inoculation there is slight motor incoordination, increase in body tone, and gasping followed by death within one minute under complete muscular relaxation. At these doses there are either no observable convulsions or they last only 1-2 seconds at the most.

At a dose of 50 mg/kg there is slight tail stiffening, dyspnea and gasping, loss of posture, weak contractions of the rear limbs every 5-10 seconds, slight foamy salivation, exophthalmos and lacrimation. Death occurs within a few minutes. In the surviving animals the initial convulsions are more evident, with an initial stiffening of the tail and of the rear limbs followed by brief jumping and tonic convulsions. Touching equally leads to tonic-clonic convulsions. At the lower doses of 40 and 30 mg/kg the initial tonic convulsions are more evident, with Straub tail, extension of the rear limbs and contraction of the front limbs, arching of the back, dyspnea and increase in abdominal tone. In some animals death occurs after about 10 minutes. Even at the lowest dose of 20 mg/kg the initial tonic convulsions are still well evident although of shorter duration, and Straub tail, hypertonic effect and motor incoordination are observed.

After about one hour following treatment, behaviour is still not completely normal, with pilo-reaction, poor spontaneous motor activity and behaviour, increase in abdominal tone, abnormal walking and central analgesia, whereas salivation, lacrimation or exophthalmos are not observed, and reaction to touch is normal. After about 6 hours following treatment a certain sedation persists, with reduced spontaneous activity and disordered fur, but no central analgesic activity is observed.

Oral and subcutaneous administration

The symptomatology observed is analogous to that described for compound 3. At a dose of 1000 mg/kg mortality is observed between the 6th and 10th hour. After about 6 hours following treatment the surviving animals still show psychomotor excitement, with Straub tail, abnormal walking, central analgesia, and hypertonic rear limbs. Even at lower doses Staub tail is present, with fur slightly in disorder, immobility and/or abnormal walking.

Good analgesic activity persists after about 6 hours following treatment.

CONCLUSIONS

All the examined compounds have almost identical toxicity for intravenous administration, and only compound 3 appears slightly less toxic than the others, even though it is more active in its observed effects for equal doses. For oral and subcutaneous administration three compounds have almost the same toxicity (1, 2, 4) at around 1000 mg/kg, and the others (0 and 3) are at least twice as toxic.

The activity of these compounds at high doses mainly affects the cardio-respiratory system (blockage), this being the main cause of death. At sublethal doses, tonic convulsions and action directed towards the C.N.S. are more manifest. At the lowest doses, where toxic action is less manifest, analgesic activity is always noted.

In general, oral administration appears more toxic than subcutaneous, and better shows up all the effects of the products. Mortality is always observed within 24 hours and generally within the first minutes, but sometimes after some hours following treatment.

TABLE 3

Acute toxicity in the CD-1 mouse (approximate $LD_{50}$ by the Irving test)*
$LD_{50}$ values in mg/kg

| Compound | oral | Method of administration | |
|---|---|---|---|
| | | subcutaneous | intravenous |
| 0 | 400 | 625 | 50 |
| 1 | >1000 | >1000 | 50 |
| 2 | >1000 | >1000 | 50 |
| 3 | 350 | 550 | 55 |
| 4 | 925 | >1000 | 50 |

*These values can be considerably different from those which can appear from a normal acute toxicity test.

I claim:

1. Compounds of formula:

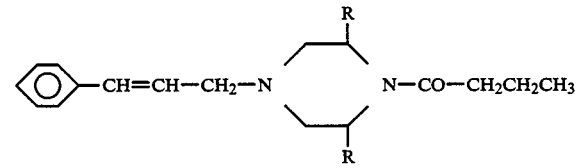

where R is H or methyl, at least one R being methyl, and the corresponding salts obtained by salifying the basic compound with a therapeutically acceptable acid.

2. A therapeutic composition with both central and peripheral analgestic activity, consisting essentially of an analgesically effective amount of a compound according to claim 1 and a pharmaceutically acceptable carrier.

* * * * *